United States Patent
Bromidge et al.

(10) Patent No.: US 6,369,060 B1
(45) Date of Patent: *Apr. 9, 2002

(54) INDOLINE DERIVATIVES USEFUL AS 5-HT-2C RECEPTOR ANTAGONISTS

(75) Inventors: Steven Mark Bromidge, Sawbridgeworth; Ian Thomson Forbes, Stevenage, both of (GB)

(73) Assignee: SmithKline Beecham p.l.c., Brentford (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/202,780

(22) PCT Filed: Jun. 16, 1997

(86) PCT No.: PCT/EP97/03156

§ 371 Date: Dec. 21, 1998

§ 102(e) Date: Dec. 21, 1998

(87) PCT Pub. No.: WO97/48699

PCT Pub. Date: Dec. 24, 1997

(30) Foreign Application Priority Data

Jun. 20, 1996 (GB) .................................. 9612883

(51) Int. Cl.[7] .................... A61K 31/501; A61K 31/444; C07D 401/14
(52) U.S. Cl. .................. 514/252.03; 514/333; 544/238; 546/256
(58) Field of Search .................. 544/238; 546/256; 514/253, 333, 253.02

(56) References Cited

U.S. PATENT DOCUMENTS 5,990,133 A * 11/1999 Gaster et al. ............. 514/337
6,028,085 A * 2/2000 Bromidge ................. 514/333

FOREIGN PATENT DOCUMENTS

| WO | WO 89/01333 | 2/1989 |
| WO | WO 94/04533 | 3/1994 |
| WO | WO 95/01976 | 1/1995 |
| WO | WO 96/23783 | 8/1996 |
| WO | 9737989 | * 10/1997 |
| WO | 9804289 | * 2/1998 |

* cited by examiner

*Primary Examiner*—Emily Bernhardt
(74) *Attorney, Agent, or Firm*—Soma G. Simon; William T. King; Charles M. Kinzig

(57) ABSTRACT

The invention relates to compounds of formula (I) or a salt thereof

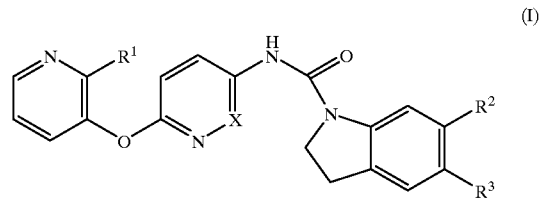

wherein X is CH or N; $R^1$ is hydrogen or $C_{1-6}$ alkyl; $R^2$ and $R^3$ groups are independently $C_{1-6}$ alkyl, or trifluoromethyl, having pharmacological activity, processes for their preparation, compositions containing them and to their use in the treatment of CNS disorders such as anxiety.

11 Claims, No Drawings

INDOLINE DERIVATIVES USEFUL AS 5-HT-2C RECEPTOR ANTAGONISTS

This invention relates to compounds having pharmacological activity, processes for their preparation, to compositions containing them and to their use in the treatment of CNS disorders.

PCT/EP96/00368 (WO-A-96/23783, 08.08.96) (SmithKline Beecham plc) describes indole and indoline derivatives which are described as possessing $5HT_{2C/2B}$ receptor antagonist activity. A novel class of compounds has now been discovered which fall within the generic scope of PCT/EP96/00368, but are not specifically disclosed therein, and have been found to exhibit a surprisingly enhanced $5HT_{2C}$ receptor antagonist activity profile (enhanced activity and duration of action after oral dosing). $5HT_{2C}$ receptor antagonists are believed to be of potential use in the treatment of CNS disorders such as anxiety, depression, epilepsy, obsessive compulsive disorders, migraine, Alzheimers disease, sleep disorders, feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI (gastrointestinal) disorders such as IBS (Irritable Bowel Syndrome) as well as microvascular diseases such as macular oedema and retinopathy.

The present invention therefore provides, in a first aspect, a compound of formula (I) or a salt thereof:

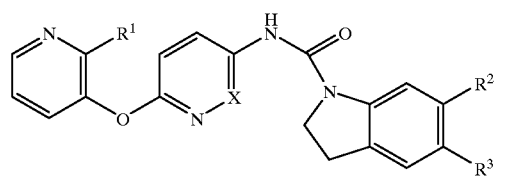

(I)

wherein:

X is CH or N;

$R^1$ is hydrogen or $C_{1-6}$ alkyl;

$R^2$ and $R^3$ groups are independently $C_{1-6}$ alkyl or trifluoromethyl.

$C_{1-6}$ Alkyl groups, whether alone or as part of another group, may be straight chain or branched.

Preferably X is CH.

Preferably $R^1$ is methyl.

Preferably $R^2$ is $CF_3$ (trifluoromethyl).

Preferably $R^3$ is $C_{1-6}$ alkyl, particularly methyl.

Particular compounds of the invention include: 5-Methyl-6-trifluoromethyl-1-[6-(2-methylpyridin-3-yloxy)-pyridin-3-ylcarbamoyl]indoline. This compound can also be named as 5-Methyl-1-[2-(2-methylpyridin-3-yloxy)-5-pyridylcarbamoyl]-6-trifluoromethylindoline or 2,3-Dihydro-5-methyl-N-[2-(2-methyl-3-pyridinyl)oxy]-5-pyridinyl]-6-(trifluoromethyl)-1H-indole-1-carboxamide, 5-Methyl-1-[6-(2-methylpyridin-3-yloxy)-pyridazin-3-ylcarbamoyl]-6-trifluoromethylindoline, and pharmaceutically acceptable salts thereof.

The compounds of the formula (I) can form acid addition salts with acids, such as conventional pharmaceutically acceptable acids, for example maleic, hydrochloric, hydrobromic, phosphoric, acetic, fumaric, salicylic, citric, lactic, mandelic, tartaric and methanesulphonic acids. A particularly preferred salt is 5-Methyl-6-trifluoromethyl-1-[6-(2-methylpyridin-3-yloxy)-pyridin-3-ylcarbamoyl]indoline monohydrochloride.

Compounds of formula (I) may also form N-oxides or solvates such as hydrates, and the invention also extends to these forms. The invention also extends to any tautomeric forms of the compounds of formula (I) and mixtures thereof. When referred to herein, it is understood that the term 'compound of formula (I)' also includes all these forms. The compounds of the invention can be prepared using standard procedures such as those of PCT/EP96/00368 (WO-A-96/23783), for example by the coupling of a compound of formula (II);

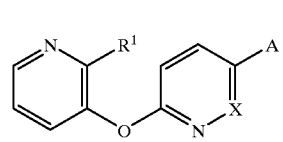

(II)

with a compound of formula (III);

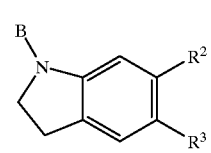

(III)

in which $R^1$, $R^2$ and $R^3$ are as defined in formula (I) and A and B contain the appropriate functional group(s) necessary to form the moiety —NHCO— when coupled and thereafter optionally forming a pharmaceutically acceptable salt thereof Suitable examples of groups A and B include:

(i) A is —N=C=O and B is hydrogen, (ii) A is —NHCOL and B is hydrogen, (iii) A is —NH$_2$ and B is COL, or (iv) A is halogen and B is —CONH$_2$ wherein L is a leaving group. Examples of suitable leaving groups L include halogen such as chloro or bromo, imidazole, or phenoxy or phenylthio optionally substituted, for example, with halogen.

Preferably A is —NHCOL and B is hydrogen; particularly preferably A is —NHCOOPh and B is hydrogen.

Compounds of formula (II) and (III) may be prepared according to known methods or analogous to known methods and to methods described in the following descriptions, for example using the procedures described in WO 95/01976 and PCT/EP96/00368 (WO-A-96/23783).

Novel intermediates of formula (II) also form part of the invention.

Pharmaceutically acceptable salts may be prepared conventionally by reaction with the appropriate acid or acid derivative. N-oxides may be formed conventionally by reaction with hydrogen peroxide or percarboxylic acids.

Compounds of formula (I) and their pharmaceutically acceptable salts have $5HT_{2C}$ receptor antagonist activity and are believed to be of potential use for the treatment or prophylaxis of CNS disorders such as anxiety, depression, epilepsy, obsessive compulsive disorders, migraine, Alzheimers disease, sleep disorders (including disturbances of Circadian rhythm), feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI disorders such as IBS as well as microvascular diseases such as macular oedema and retinopathy.

Thus the invention also provides a compound of formula (I) or a pharmaceutically acceptable salt thereof, for use as a therapeutic substance, in particular in the treatment or prophylaxis of the above disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for the treatment or prophylaxis of the above disorders.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.5 to 100 mg; and such therapy may extend for a number of weeks or months.

When administered in accordance with the invention, no unacceptable toxicological effects are expected with the compounds of the invention.

The following Descriptions and Examples illustrate the preparation of compounds of the invention.

DESCRIPTION 1

(5-Methoxy-2-nitro-4-trifluoromethylphenyl)acetonitrile (D1)

A mixture of 1-methoxy-4-nitro-2-trifluoromethylbenzene (93 g, 0.421 mol) and 4-chlorophenoxyacetonitrile (77.55 g, 0.463 mol) in dry DMF (500 ml) was added dropwise over 0.75 h to a stirred solution of KO$^t$Bu (103.85 g, 0.927 mol) in dry DMF (400 ml) at −10° C. After complete addition the resulting purple solution was maintained at −10° C. for 1 h then poured into a mixture of ice/water (1.5 l) and 5 M aqueous HCl (1.5 l). The resulting mixture was extracted with dichloromethane (3×1 l). The combined extracts were washed with water (3 l), dried (Na$_2$SO$_4$) and evaporated under reduced pressure. The residue was chromatographed on silica using 10–40% ethyl acetate/petroleum ether as eluant to give the crude product which was recrystallised from ethyl acetate/petroleum ether to afford the title compound (85.13 g, 78%) as a white solid. Mp 103–104° C.

$^1$H NMR (CDCl$_3$) δ: 4.10 (3H, s), 4.37 (2H, s), 7.34 (1H, s), 8.53 (1H, s).

DESCRIPTION 2

5-Methoxy-6-trifluoromethylindole (D2)

(5-Methoxy-2-nitro-4-trifluoromethylphenyl)acetonitrile (D1) (85 g, 0.327 mol) in ethanol/water (9:1, 1.6 l) and glacial acetic acid (16 ml) was hydrogenated over 10% palladium on carbon (50 g) at 50 psi for 0.5 h at room temperature. The reaction mixture was filtered and evaporated in vacuo. The residue was partitioned between aqueous K$_2$CO$_3$ (1 l) and dichloromethane (2×1 l) and the combined organic extract was dried (Na$_2$SO$_4$) and evaporated to afford the title indole (67.63 g, 96%) as a grey solid.

$^1$H NMR (CDCl$_3$) δ: 3.94 (3H, s), 6.53 (1H, m), 7.21 (1H, s), 7.32 (1H, m), (1H, s), 8.25 (1H, br s).

DESCRIPTION 3

5-Methoxy-6-trifluoromethylindoline (D3)

The indole (D2) (67.63 g, 0.315 mol) in glacial acetic acid (500 ml) was treated with sodium cyanoborohydride (40 g, 0.637 mol) portionwise at room temperature with stirring. After 3 h at room temperature the reaction mixture was diluted with water (500 ml) and basified with 40% aqueous NaOH with cooling. The mixture was then extracted with dichloromethane (3×500 ml) and the combined extracts were dried (Na$_2$SO$_4$) and evaporated to give the title compound (67.73 g, 99%) as an off-white solid.

$^1$H NMR (CDCl$_3$) δ: 3.07 (2H, t), 3.58 (2H, t), 3.67 (1H, br s), 3.83 (3H, s), 6.83 (1H, s), 6.88 (1H, s).

DESCRIPTION 4
5-Hydroxy-6-trifluoromethylindoline (D4)

A mixture of 5-methoxy-6-trifluoromethylindoline (D3, 7.5 g, 34.3 mmol) and iodotrimethylsilane (12.5 ml, 89.3 mmol) in dry chloroform (70 ml) was heated under reflux for 65 h. Methanol was then added cautiously with stirring to the cooled mixture, and solvent was then removed in vacuo. The residue was treated with saturated sodium bicarbonate solution and water until basic, and then extracted with dichloromethane/methanol. The organic extract was washed with brine, dried and evaporated. The residue was extracted with ether in a Soxhlet apparatus, and concentration of the resultant solution gave the title compound in three crops (total 2.85 g, 41%), m.p.>180° (decomp.).

$^1$H NMR (CDCl$_3$/CD$_3$OD) δ: 3.02 (2H, d, J=8), 3.52 (2H, d, J=8), 4.00 (3H, s), 6.77 (1H, s), 6.83 (1H, s).

DESCRIPTION 5
1-Acetyl-5-hydroxy-6-trifluoromethylindoline (D5)

A mixture of indoline (D4, 2.84 g, 14 mmol) and acetic anhydride (1.32 ml, 14 mmol) in dry dichloromethane (50 ml) was stirred at room temperature for 3 h, then evaporated. The residue was treated cautiously with saturated sodium bicarbonate solution, then the solid product was filtered off, washed with water and dried to give the title compound (3.28 g, 96%), m.p. 244–7° C.

$^1$H NMR (d$_6$-DMSO) δ: 2.10 (3H, s), 3.11 (2H, t, J=8), 4.06 (2H, t, J=8), 6.88 (1H, s), 8.18 (1H, s).

DESCRIPTION 6
1-Acetyl-6-trifluoromethyl-5-trifluoromethylsulphonyloxy-indoline (D6)

To a solution of the acetylindoline (D5, 1.19 g, 4.9 mmol) in dry pyridine (10 ml) at 0° C. was added trifluoromethane-sulphonic anhydride (1.52 g, 5.4 mmol). The mixture was then stirred overnight, while slowly warming to room temperature. The mixture was partially evaporated, the residual liquor was diluted well with water and the precipitate was filtered off. The crude product was dissolved in dichloromethane and the solution was washed with 1N hydrochloric acid and brine, dried and evaporated to give the title compound (1.77 g, 96%).

$^1$H NMR (CDCl$_3$) δ: 2.28 (3H, s), 3.32 (2H, t, J=8), 4.19 (2H, t, J=8), 7.29 (1H, s, 8.60 (1H, s). MS m/z=378 (MH$^+$).

DESCRIPTION 7
5-Methyl-6-trifluoromethylindoline (D7)

To a mixture of the trifluoromethylsulphonyloxyindoline (D6, 1.77 g, 4.69 mmol), lithium chloride (0.60 g, 14.1 mmol) and bis(triphenylphosphine) palladium (II) chloride (0.10 g, 0.14 mmol) in dry dimethylformamide (15 ml) was added tetramethyltin (0.72 ml, 5.2 mmol). The mixture was heated at 110° C. for 3.5 h, then cooled and evaporated. The residue was partitioned between dichloromethane and water, and the organic phase was washed with brine, dried and evaporated. The crude product was dissolved in ethanol (30 ml), 10% aqueous sodium hydroxide solution (7.5 ml) and solid sodium hydroxide (1 g) were added and the mixture was heated under reflux overnight. Ethanol was removed in vacuo, and the residue was diluted with water and extracted with dichloromethane. The organic extract was washed with brine, dried and evaporated. The residue was chromatographed on silica gel (50 g), eluted under suction with 2:1 ether/petroleum ether to give the title compound (0.70 g, 74%), m.p. 43–4° C.

$^1$H NMR (CDCl$_3$) δ: 2.34 (3H, s), 3.02 (2H, t, J=8), 3.57 (2H, t, J=8), 3.78 (1H, broad), 6.85 (1H, s), 7.00 (1H, s).

DESCRIPTION 8
2-(2-Methylpyridin-3-yloxy)-5-nitropyridine (D8)

3-Hydroxy-2-methylpyridine (40 g, 0.37 mole) in dry DMF (1.3 L) under argon was cooled to 0° C. Sodium hydride (11.1 g of an 80% dispersion in oil, 0.37 mole) was added portionwise and the mixture stirred at 0° C. for 15 minutes and then room temperature for 3 hours. 2-Chloro-5-nitropyridine (58.6 g, 0.37 mole) was added and the mixture stirred for 18 hours at r.t. Water (50 ml) was added dropwise and the solvent was removed in vacuo. The residue was dissolved in CH$_2$Cl$_2$, washed with 10% aqueous sodium hydroxide, and water, dried (Na$_2$SO$_4$) and evaporated in vacuo to afford the title compound (81.1 g, 95%) as a yellow solid.

$^1$H NMR (200 MHz; CDCl$_3$) δ(ppm): 2.22 (3H, s), 6.93 (1H, d, J=8), 7.00–7.13 (1H, m), 7.23 (1H, dd, J=1, 8), 8.25 (1H, dd, J=1,5), 8.32 (1H, dd, J=3,8), 8.79 (1H, d, J=3).

DESCRIPTION 9
5-Amino-2-(2-methylpyridin-3-yloxy)pyridine (D9)

2-(2-Methylpyridin-3-yloxy)-5-nitropyridine (D8, 81.1 g, 0.35 mole) in ethanol (2L) was treated with tin (II) chloride (232 g, 1.23 mole) in conc. hydrochloric acid (500 ml) and heated to 50° C. for 1 hour. After cooling to ambient temperature, the mixture was basified with 40% aqueous sodium hydroxide solution, extracted into ethyl acetate, dried (Na$_2$SO$_4$) and evaporated in vacuo to afford the title compound (60.3 g, 86%) as a brown solid.

$^1$H NMR (200 MHz; CDCl$_3$) δ(ppm): 2.26 (3H, s), 3.40 (2H, br s), 6.56 (1H, d, J=9), 6.81–6.97 (2H, m), 7.08 (1H, dd, J=1,5), 7.43 (1H, d, J=3), 8.09 (1H, dd, J=1,4).

DESCRIPTION 10
Phenyl N-[2-(2-methylpyridin-3-yloxy)pyridin-5-yl] carbamate (D10)

5-Amino-2-(2-methylpyridin-3-yloxy)pyridine (D9, 60.3 g, 0.3 mole) in dry CH$_2$Cl$_2$ (2.5L) was cooled to −20° C. under argon. Triethylamine (46 ml, 0.33 mole) was added, followed dropwise by phenyl chloroformate (41 ml, 0.33 mole) and the mixture was stirred at −20° C. for 1 hour. After warming to ambient temperature, the mixture was washed with dil. aq. NaHCO$_3$, dried (Na$_2$SO$_4$) and evaporated in vacuo. The residue was recrystallised from ethyl acetate/60–80° petroleum ether to afford the title compound (53.7 g, 56%) as a pink solid.

$^1$H NMR (250 MHz; CDCl$_3$) δ(ppm): 2.44 (3H, s),6.94 (1H, d, J=7), 7.08–7.29 (4H, m), 7.33–7.45 (3H, m), 7.90 (1H, br s), 7.98–8.13 (2H, m), 8.39 (1H, d, J=5).

DESCRIPTION 11
6-(2-Methylpyridin-3-yloxy)pyridazine-3-carboxylic acid ethyl ester (D11)

Sodium hydride (0.21 g of an 80% dispersion in oil, 7.0 mmol) was added to a solution of 3-hydroxy-2-methylpyridine (0.88 g, 8.0 mmol) in DMF (15 ml). After 1.5 h at r.t. a solution of 6-chloropyridazine-3-carboxylic acid ethyl ester (*Chem. Pharm. Bull.* 1994, 42(2), 371) (1.0 g, 5.4 mmol) in DMF (10 ml) was added and the mixture was stirred for a further 1.5 h. The DMF was removed in vacuo and the residue partitioned between dil. aq. NaOH (50 ml) and CH$_2$Cl$_2$ (100 ml). After drying (Na$_2$SO$_4$) the organics were evaporated to give the title compound as an off-white solid (1.09 g, 78%).

$^1$H NMR (250 MHz, CDCl$_3$) δ: 1.46 (3H, t, J=7), 2.45 (3H, s), 4.50 (2H, q, J=7), 7.22 (1H, dd, J=4), 7.37 (1H, d, J=10), 7.51 (1H, d, J=10), 8.26 (1H, d, J=10), 8.45 (1H, dd, j=2,7).

DESCRIPTION 12
6-(2-Methylpyridin-3-yloxy)piperazine-3-carboxylic acid hydrazide (D12)

6-(2-Methylpyridin-3-yloxy)-pyridazine-3-carboxylic acid ethyl ester (D11) (1.07 g, 4.13 mmol) and hydrazine monohydrate (0.23 ml, 7.22 mmol) in ethanol (100 ml) was stirred at room temperature for 1 hour then heated at 50° C. for 1 hour and finally heated at reflux for 4 hours. A second portion of hydrazine monohydrate (0.23 ml, 7.22 mmol) was added and the mixture refluxed for a further 2 hours. After being allowed to cool the solvent was removed in vacuo. The off-white solid residue was subjected to column chromatography using 25% MeOH/EtOAc as eluant, resulting in a white crystalline product (0.63 g, 62%).

$^1$H NMR (200 MHz, CDCl$_3$) δ: 2.43 (3H, s), 4.09 (2H, d, J=5), 6.91 (1H, br s), 7.42 (1H, d, J=11), 7.50 (1H, dd, J=2,8), 8.33 (1H, d, J=10), 8.47 (1H, dd, J=2,5), 8.66 (1H, m).

DESCRIPTION 13
6-(2-Methylpyridin-3-yloxy)-pyridazine-3-carbonyl azide (D13)

A solution of 6-(2-methylpyridin-3-yloxy)-pyridazine-3-carboxylic acid hydrazide (D12) (0.62 g, 2.53 mmol) in conc. hydrochloric acid (9 ml) and water (7.5 ml) cooled to 0° C. in an ice-bath was treated with a solution of sodium nitrite (0.18 g, 2.53 mmol) in water (1.5 ml) dropwise keeping the temperature below 5° C. After 10 minutes saturated potassium carbonate was added until basic. The precipitate was filtered off, washed with water and air dried to give a cream solid (0.33 g, 51%).

$^1$H NMR (200 MHz, CDCl$_3$) δ(ppm): 2.46 (3H, s), 7.24 (1H, d, J=5), 7.40 (1H, d, J=10), 7.53 (1H, dd, J=1,8), 8.30 (1H, d, J=10), 8.49 (1H, dd, J=1,8).

EXAMPLE 1
5-Methyl-6-trfluoromethyl-1-[6-(2-methylpyridin-3-yloxy)-pyridin-3-ylcarbamoyl]indoline (E1)

A mixture of indoline (D7, 20 g, 99.5 mmol), phenylcarbamate (D10, 31.9 g, 99.5 mmol) and triethylamine (13.9 ml, 100 mmol) in dry dimethylformamide (1L) was heated at 95–105° C. for 1 h, then cooled and evaporated in vacuo. The residue was diluted with dichloromethane and washed with 10% aqueous sodium hydroxide, with addition of methanol to keep the product in solution. The organic phase was washed with water and brine, dried and evaporated. The crude product was recrystallised from dichloromethane to give the title compound (32.5 g, 76%), m.p. 112–4° C.

$^1$H NMR (d$_6$-DMSO) δ: 2.32 (3H, s), 2.38 (3H, s), 3.22 (2H, d, J=8), 4.16 (2H, d, J=8), 7.09 (1H, d, J=8), 7.25 (1H, s), 7.30 (1H, dd, J=8,5), 7.49 (1H, d, J=8), 8.06 (1H, dd, J=8,2), 8.16 (1H, s), 8.20 (1H, d, J=2), 8.31 (1H, d, J=5), 8.78 (1H, s).

EXAMPLE 2
5-Methyl-6-trifluoromethyl-1-[6-(2-methylpyridin-3-yloxy)-pyridin-3-ylcarbamoyl]indoline hydrochloride (E2)

To a stirred suspension of the free-base (E1, 32.5 g, 75.9 mmol) in methanol (1L) was added a solution of hydrochloric acid (S.G. 1.18, 7 mL, 84 mmol) in methanol (50 mL) dropwise over 15 mins. The resulting solution was concentrated in vacuo to approximately half the original volume, then boiled down further on a steam-bath with addition of ether until cloudiness persisted. The solution was cooled, finally in ice, and the precipitate was filtered off, washed with ether and dried to give the title compound (33.8 g, 96%) as a white solid, m.p. 241–6° C.

$^1$H NMR (d$_6$-DMSO) δ: 2.35 (3H, s), 2.58 (3H, s), 3.23 (2H, d, J=8), 4.20 (2H, d, J=8), 7.24 (1H, d, J=8), 7.26 (1H, s), 7.83 (1H, dd, J=8,5), 8.15 (1H, s), 8.18 (1H, m), 8.21 (1H, d, J=8), 8.32 (1H, d, J=2), 8.51 (1H, d, J=8), 9.00 (1H, s).

The title compound can also be prepared by treating a solution of the free base in propanol with concentrated hydrochloric acid.

EXAMPLE 3
5-Methyl-6-trifluoromethyl-1-[6-(2-methylpyridin-3-yloxy)-pyridin-3-ylcarbamoyl]indoline methyl sulphonate (E3)

The free-base (E1, 2 g, 4.7 mmol) in refluxing 3% aqueous acetone (50 ml) was treated with methanesulphonic acid (0.47 g). The resulting solution was concentrated in vacuo and taken up in boiling methanol (50 ml) then boiled down further on a steam-bath with addition of ether until precipitation began. The solution was cooled, finally in ice, and the precipitate was filtered off, washed with ether and dried to give the title compound (2.35 g, 96%) as a white solid, m.p. 159–161° C.

$^1$H NMR (d$_6$-DMSO) δ: 2.35 (3H, s), 2.38 (3H, s), 2.50 (3H, s), 3.23 (2H, d, J=8), 3.89 (1H, br s), 4.18 (2H, d, J=8), 7.23 (1H, d, J=8), 7.28 (1H, s), 7.79 (1H, dd, J=8,5), 8.10–8.18 (3H, m), 8.29 (1H, d, J=2), 8.51 (1H, d, J=8), 8.85 (1H, s).

EXAMPLE 4
5-Methyl-1-[6-(2-methylpyridin-3-yloxy)-pyridazin-3-ylcarbamoyl]-6-trifluoromethylindoline (E4)

A solution of 6-(2-methylpyridin-3-yloxy)pyridazine-3-carbonyl azide (D13) (0.33 g, 1.29 mmol) and 5-methyl-6-trifluoromethylindoline (D7) (0.26 g, 1.29 mmol) in toluene (20 ml) was heated at 100° C. for 1 hour, then allowed to cool. The solvent was removed in vacuo to leave a pale brown solid. This was subjected to column chromatography using 5% MeOH/DCM as eluant and the product recrystallised from EtOAc/pet. ether to give a white powder (0.30 g, 54%) m.p. 216–217° C.

$^1$H NMR (250 MHz, CDCl$_3$) δ(ppm): 2.42 (3H, s), 2.47 (3H, s), 3.25 (2H, t, J=10), 4.16 (2H, t, J=10), 7.10 (1H, s), 7.19 (1H, dd, J=5,8), 7.29 (1H, d, J=10), 7.46 (1H, dd, J=2,6), 7.91 (1H, br. s), 8.27 (1H, s), 8.38 (1H, dd, J=2,6), 8.48 (1H, d, J=10).

Pharmacological Data

[$^3$H]-mesulergine binding to rat or human 5-HT$_{2C}$ clones expressed in 293 cells in vitro Compounds can be tested following the procedure outlined in WO 94/04533. The compounds of the Examples had pKi values of about 8.6 to 9.5 in human cells.

Reversal of MCPP-induced Hypolocomotion

Compounds can be tested following the procedure outlined in WO 94/04533. The compounds of the examples showed good activity after dosing at 1–5 mg/kg p.o. in the rat with an extended duration of action.

What is claimed is:

1. A compound of formula (I) or a pharmaceutically acceptable acid addition salt thereof:

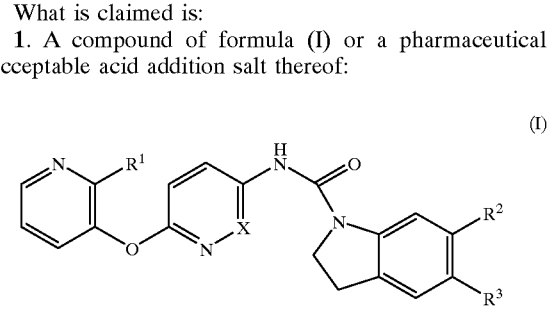

wherein:

X is CH or N;

$R^1$ is hydrogen or $C_{1-6}$ alkyl;

$R^2$ and $R^3$ groups are independently $C_{1-6}$ alkyl or trifluoromethyl.

2. A compound according to claim 1 in which X is CH.

3. A compound according to claim 1 in which $R^1$ is methyl.

4. A compound according to claim 3 in which $R^2$ is $CF_3$.

5. A compound according to claim 4 in which $R^3$ is $C_{1-6}$ alkyl.

6. A compound according to claim 5 in which $R^3$ is methyl.

7. A compound according to claim 1 which is:

5-Methyl-6-trifluoromethyl-1-[6-(2-methylpyridin-3-yloxy)-pyridin-3-ylcarbamoyl]indoline, 5-Methyl-6-trifluoromethyl-1-[6-(2-methylpyridin-3-yloxy)-pyridazin-3-ylcarbamoyl]indoline, or a pharmaceutically acceptable salt thereof.

8. A compound according to claim 1 which is 5-Methyl-6-trifluoromethyl-1-[6-(2-methylpyridin-3-yloxy)-pyridin-3-ylcarbamoyl]indoline hydrochloride.

9. A process for preparing a compound according to claim 1 which comprises reacting a compound of formula (II);

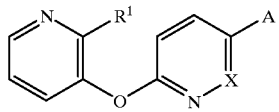

(II)

with a compound of formula (III);

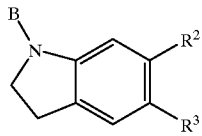

(III)

in which $R^1$, $R^2$ and $R^3$ are as defined in formula (I) and A and B have the following meanings:

(i) A is —N=C=O and B is hydrogen, (ii) A is —NHCOL and B is hydrogen, (iii) A is —$NH_2$ and B is COL, or (iv) A is halogen and B is —$CONH_2$ wherein L is a leaving group, and thereafter optionally forming a pharmaceutically acceptable salt thereof.

10. A pharmaceutical composition which comprises a compound according to claim 1 and a pharmaceutically acceptable carrier or excipient.

11. A method of treating anxiety or depression comprising administering a therapeutically effective amount of a compound according to claim 1.

* * * * *